(12) United States Patent
Dolan, II et al.

(10) Patent No.: US 11,420,461 B2
(45) Date of Patent: Aug. 23, 2022

(54) DRUM STENCIL PRINTING SYSTEM

(71) Applicant: Smart Cups, LLC, Mission Viejo, CA (US)

(72) Inventors: Owen J. Dolan, II, Trabuco Canyon, CA (US); Chris Kanik, Ladera Ranch, CA (US); William F. Davidson, III, Laguna Niguel, CA (US); John Depiano, Burlington, MA (US); Mark Clemons, Weston, MA (US); Gary Ayotte, Newburyport, MA (US); Frank S. Silveira, Wilmington, MA (US); Michael Marcoux, Jamaica Plain, MA (US); Matthew Ebbs, Natick, MA (US)

(73) Assignee: SMART CUPS, LLC, Mission Viejo, CA (US)

( * ) Notice: Subject to any disclaimer, the term of this patent is extended or adjusted under 35 U.S.C. 154(b) by 64 days.

(21) Appl. No.: 16/816,182

(22) Filed: Mar. 11, 2020

(65) Prior Publication Data

US 2021/0283933 A1 Sep. 16, 2021

(51) Int. Cl.
*B41L 13/06* (2006.01)
*B41M 1/12* (2006.01)

(52) U.S. Cl.
CPC ............... *B41L 13/06* (2013.01); *B41M 1/12* (2013.01)

(58) Field of Classification Search
CPC .......... B41F 15/18; B41F 15/30; B41F 15/32; B41F 15/38; B41F 15/40; B41F 15/42; B41F 15/44; B41F 15/405; B41F 15/0872; B41F 15/0881; B41F 17/00; B41F 17/001; B41F 17/002; B41F 17/003; B41F 17/006; B41F 17/08; B41F 17/10; B41F 17/18; B41F 17/22; B41F 17/26; B41F 17/28;
(Continued)

(56) References Cited

U.S. PATENT DOCUMENTS 2,071,336 A * 2/1937 Glenn ................... B65H 67/063
101/35
2,169,619 A * 8/1939 Smith ................. B41F 15/0895
101/123
(Continued)

FOREIGN PATENT DOCUMENTS

DE 2414378 * 10/1975 ............ B41F 17/006
DE 102011119808 * 6/2013 ............. B41F 17/28

*Primary Examiner* — Matthew G Marini
*Assistant Examiner* — Marissa Ferguson-Samreth
(74) *Attorney, Agent, or Firm* — West Coast IP, P.C.; Matthew D. Bottomly

(57) ABSTRACT

The present invention relates to a drum stencil printing system for reliably and automatically printing materials on the inside of a concave surface. The drum stencil printing system includes a pliable drum stencil secured in place by a stencil spring. As the printhead applies radial pressure to the drum stencil, the portion of the stencil in contact with the printhead is deflected to make contact with the container sidewall. When the printhead rotates, the portion of the stencil contacting the container sidewall also rotates to match the nozzle of the printhead. After printing is complete, the printhead retracts, and the pliable stencil is returned to its undeflected position, breaking contact between the stencil and the container, and protecting the printed material from being rubbed or worn off of the container.

20 Claims, 11 Drawing Sheets

(58) Field of Classification Search
CPC .......... B41F 17/30; B41F 17/32; B41F 17/34; B41F 17/36; B41F 17/38; B41J 3/40731; B41J 3/40733; B41M 1/12; B41M 1/40; B41P 2215/50; B41P 2217/00; B41P 2217/53; B41P 2217/61
See application file for complete search history.

(56) References Cited

U.S. PATENT DOCUMENTS

| | | | | |
|---|---|---|---|---|
| 2,548,580 | A * | 4/1951 | Bick | B05C 17/0355 101/331 |
| 2,879,740 | A * | 3/1959 | Mahon | H01K 3/005 118/721 |
| 4,667,594 | A * | 5/1987 | Eddy | B41F 17/006 101/35 |
| 4,682,182 | A * | 7/1987 | Oyama | B25J 9/1679 101/35 |
| 5,829,350 | A * | 11/1998 | Muchi | B41F 17/001 101/35 |
| 6,205,917 | B1 * | 3/2001 | Palmer | B41F 23/002 101/329 |
| 2014/0174308 | A1 * | 6/2014 | Wright | B41F 15/36 101/126 |
| 2020/0039243 | A1 * | 2/2020 | Riffe | B41J 3/40733 |

* cited by examiner

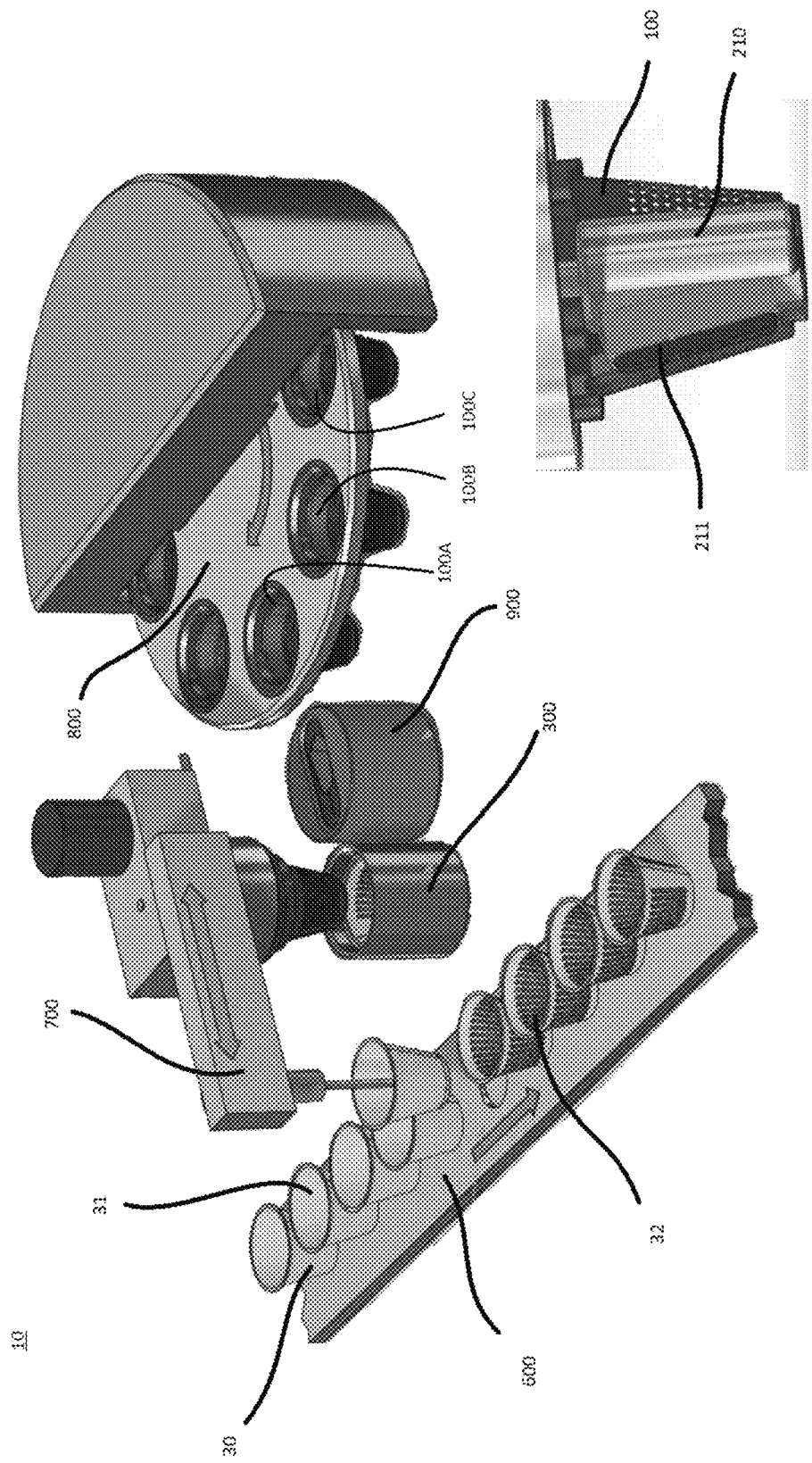

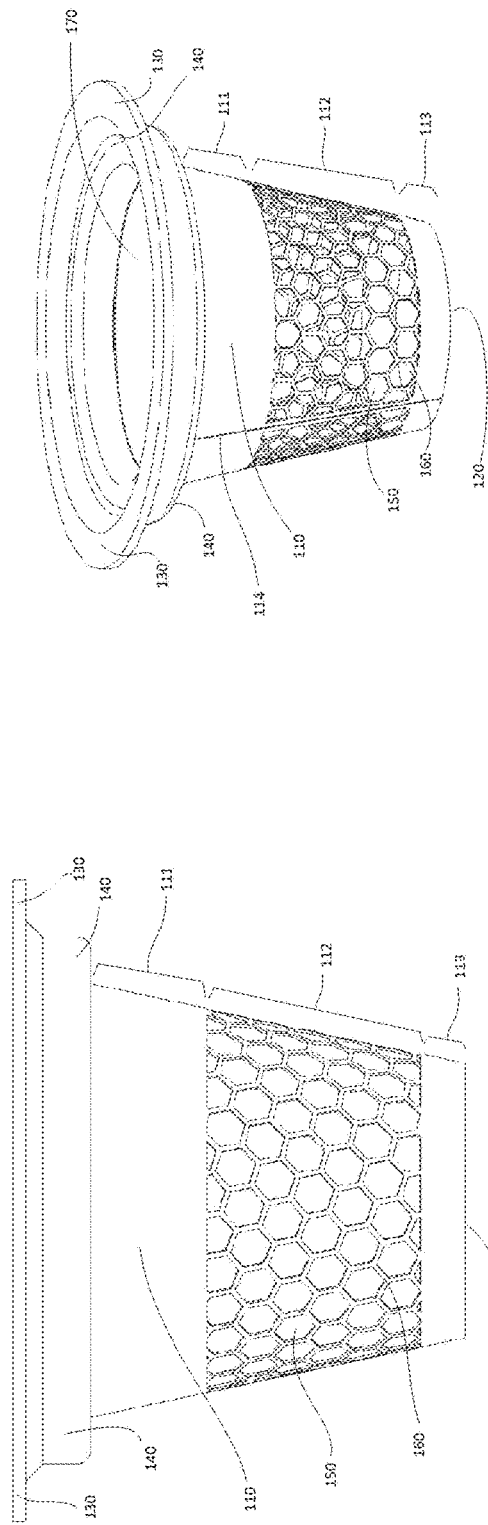
FIGURE 7A
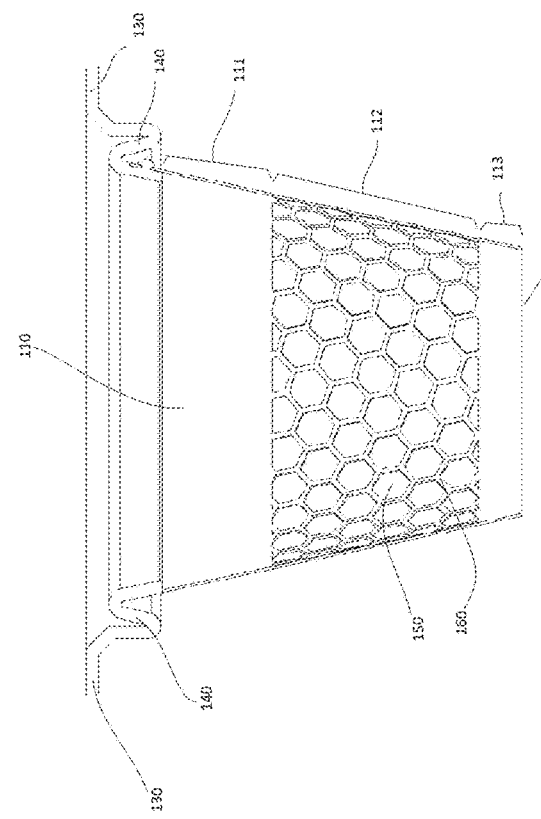
FIGURE 7B
FIGURE 7C

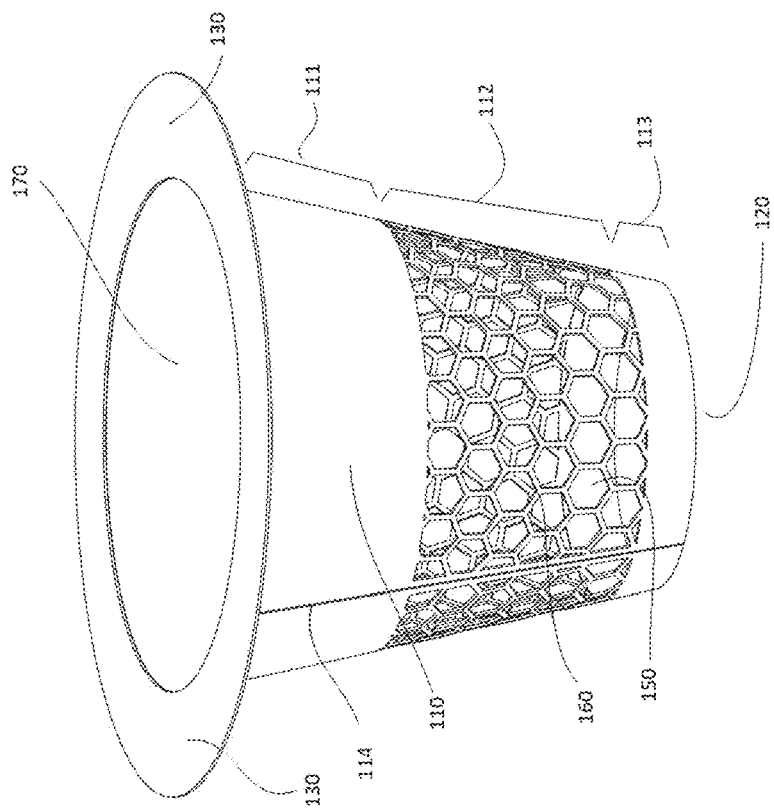
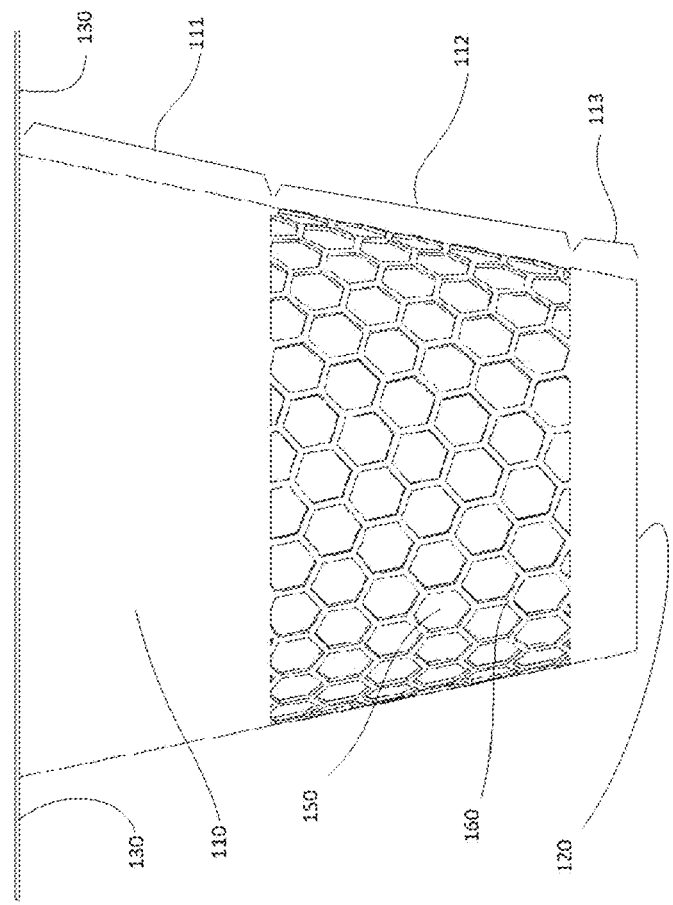
FIGURE 8B
FIGURE 8A

DRUM STENCIL PRINTING SYSTEM

CROSS-REFERENCE TO RELATED APPLICATIONS

[N/A]

FIELD OF THE INVENTION

The present invention relates generally to stencil printing. More particularly, embodiments include an apparatus for stencil printing in an automated production system. Still more particularly embodiments include an apparatus for stencil printing on the inside surface of concave objects, including containers, cups, or bowls.

DESCRIPTION OF THE RELATED ART

Modern manufacturing relies on low cost, high yield automated systems to mass produce products and reduce item cost. Stencil printing can be a low cost, high yield tool to apply ink, fluid, detail, or decoration to an object. Stencils may be used to produce large numbers of identical or similar products or to apply a large number of identical or similar details to a product.

While stencil printing is a common method for applying inks, dyes, solder paste, conductive traces, resistive elements, various electronic and semiconductor layers and components, acids and chemicals for etching or controlled chemical reactions, hydrophobic and oleophobic coatings, other types of materials do not lend themselves to traditional stencil printing. Both the material to be printed and the substrate on which the material will be printed can significantly complicate the process. In particular, applying a dry or powdered material to a dry substrate requires significant customization and modification to pump, deposit, and cure the printed materials.

Traditional stencils often require manual operation or supervision, which increases the labor cost and often produces low yield. To minimize clogs or imprecise application, many stencil systems rely on manual wash operations, during which an operator removes the stencil or stencil drum and cleans the stencil or stencil drum using baths, cleaners, scrubs, agitation, friction, or vibration between application cycles. Similarly swapping the stencil pattern often requires manual removal and replacement of the stencil or stencil drum. Both pattern swapping and wash operations typically slow the production, thereby reducing yield, increasing cycle time, or both.

Stencils are heavily used to print or extrude elements onto flat or convex surfaces, such as onto a conveyor belt, textiles, or even onto the outside surface of some objects. Applicant has recognized that there is a need therefore for a stencil printing system capable of reliably, consistently, and quickly printing on the interior or concave surface of an object within an automated production setting.

In order to address the above-described exemplary problems, and other similar problems, a novel drum stencil printing system is needed.

SUMMARY OF THE INVENTION

To address the shortcomings of existing solutions, the inventors have developed the following novel drum stencil printing system 10. Various aspects are summarized below. These aspects may be mixed as well as combined with features listed in other places in the specification, drawings, or claims in various combinations to address specific situations and requirements without departing from the current invention.

In one aspect, the drum stencil printing system 10 employs a drum stencil 100, which may be conical or cylindrical, and the drum stencil 100 may be statically mounted around a rotating internal printhead 210 and/or squeegee. The drum stencil 100 is inserted into the concave cavity of the intended printing surface or substrate 31 of the container, and the printhead 210 and/or squeegee rotate to apply the printing medium 20 through the stencil 100 around the inner surface of the printing surface 31 of a container 30 (e.g., a cup or bowl). In some embodiments, the stencil 100 is not rigid, but rather pliable or compliant. The printhead 210 and/or squeegee may extend or retract to deflect the stencil 100 to an intended print position. As the printhead 210 and/or squeegee makes contact with the pliant stencil 100, the stencil 100 deflects to make contact with the printing surface's inner sidewalls 31. After the printhead 210 or squeegee passes by a point on the stencil 100, the stencil 100 returns to its original, undeflected position, pulling away from the inner sidewall of the printing surface 31. This stencil 100 restoration allows the printing surface 31 to be removed from the stencil drum 100 without dragging or smearing the printed pattern 32 deposited on the printing surface 31.

In another aspect, the drum stencil printing system 10 enables the automated system to employ either or both of a stencil carousel 800 (see FIG. 3) and a drum wash station 900 (see FIG. 3). In further aspects, the system 10 includes the entire slurry feed system 400, including a slurry tank (or slurry mixer) 410, a slurry pump 430 (powered by slurry pump 431) to pump the slurry 20 from the tank, through slurry delivery lines 420 and to the feed tube 229 through which the slurry 20 travels from the slurry tank 410 and slurry pump 430 to the printhead.

An automated stencil printing system 10 incorporating a carousel (or alternatively a stack, line, bay, shelf, or any other type of reserve or storage area) 800 of multiple drum stencils 100 reduces reliance on human labor while switching between patterns or between slurries or liquids 20 (e.g., formulations) and eliminates downtime. As the production line finishes printing through a first stencil 100A, the automated line can quickly swap from the in-use stencil 100A to an alternate stencil 100B. The second stencil 100B may include a different pattern of apertures or islands (e.g., holes, dots, stripes, stars, hearts, leaves, or differing print depth/thickness) 150 and bridges 160 from the first stencil 100A, which enables the system 10 to quickly print either single packages including multiple different patterns or alternatively to quickly swap between producing packages that each include different patterns. Alternately, as the automated line finishes production of a first product printing a first slurry or liquid (e.g., formulations) 20A, the line can quickly swap to a different stencil drum 100 from the carousel 800 of multiple stencils 100A, 100B, 100C to begin printing a second slurry or liquid 20B without inadvertent flavor mix or flavor bleed between the two separate product types. By automatically swapping stencils 100 from the carousel 800 of available drum stencils 100, the system 10 can continuously produce products without significant delays between product types. In one specific embodiment, the system 10 may simply continuously print identical items without any downtime. In another specific embodiment, a single line incorporating a carousel 800 of stencils 100 with multiple different stencil patterns may automatically print consecutive containers, each including a different stencil print pattern of islands 150 and bridges 160. In still another specific embodiment, a single line incorporating a carousel 800 of either identical or different stencils 100 may automatically print consecutive containers 30, each including a different slurry or liquid (e.g., flavor, color, strength, or optional ingredient) 20, creating either variety packs of multiple formulations. Alternatively, these embodiments could be combined to continuously produce packages incorporating products with both rotating different ingredients and stencil patterns. As is readily apparent, a carousel 800 of multiple stencils 100 provides the automated system 10 with a number of benefits including up-time, flexibility, and variety. Another benefit of the carousel 800 of multiple drum stencils 100 is that the automated system 10 may hold a number of spare or back-up print drums 100B in reserve, in case an active drum stencil 100A fails or undesirable printed products are detected, enabling the system 10 to quickly swap the present drum stencil 100A for a back-up stencil 100B and continue production without delay.

An automated stencil printing line 10 incorporating multiple drum stencils 100—either through the above discussed carousel 800 of multiple stencils 100' or another system including multiple interchangeable stencils 100—may additionally incorporate a drum stencil wash station 900, which reduces reliance on human labor to maintain and clean the stencils 100, further eliminating downtime and enabling quick changes between flavors without intermingling product. The wash station 900 may incorporate any variety of cleaning options, including applied jet-spray (gas or liquid) or vacuum, sonication, vibration, liquid immersion, high heat to purify and clean the components, or a combination thereof. While the production line prints through a first stencil 100, the drum stencil wash station 900 may automatically clean and prepare alternate stencils for use. By automatically swapping stencils 100 through the wash station 900—either after a set number of prints, between stencil 100 swaps, between slurry or liquid (e.g., formulations) 20 changes, or in response to a detected condition, such as a clog or an undesirable print—the system 10 efficiently rotates between multiple stencils 100 without any printing down time. In some specific embodiments, the automated line may additionally include a quality control check for recognizing and removing printed items that do not meet quality control standards.

In another aspect, the system 10 may include an enclosed printhead 210 instead of a squeegee pressing the slurry 20 against the stencils 100. A traditional rotary stencil system (such as the one shown in FIG. 1) supplies a slurry or fluid supply 20 ahead of the squeegee. However, in an enclosed printhead system, the printhead instead makes direct contact with the stencil 100 and forces the fluid or slurry 20 through the nozzle 211 of the printhead 210 and directly through an aperture 150 of the stencil 100. An enclosed printhead system enables the system 10 to quickly switch on and off the slurry or liquid supply 20, reducing drippage, waste, and enabling quicker swaps between printheads 210. Additionally, a system 10 incorporating an enclosed printhead 210 enables the system 10 to take full advantage of the carousel 800 of multiple printheads 210 as well as a continuous cleaning system by minimizing waste and production delay during drum stencil 10 swaps.

BRIEF DESCRIPTION OF THE DRAWINGS

FIG. 3 is a first isometric perspective view of exemplary assembly line, automated positioning element, stencil wash station, and stencil carousel for use in the drum stencil printing system.

FIGS. 7A, 7B, and 7C are side, perspective, and cross-section views respectively of an exemplary drum stencil incorporating a stencil spring for use in the drum stencil printing system.

FIGS. 8A and 8B are side and perspective views respectively of an exemplary drum stencil that does not incorporate a stencil spring for use in the drum stencil printing system.

DETAILED DESCRIPTION

Figure 1:
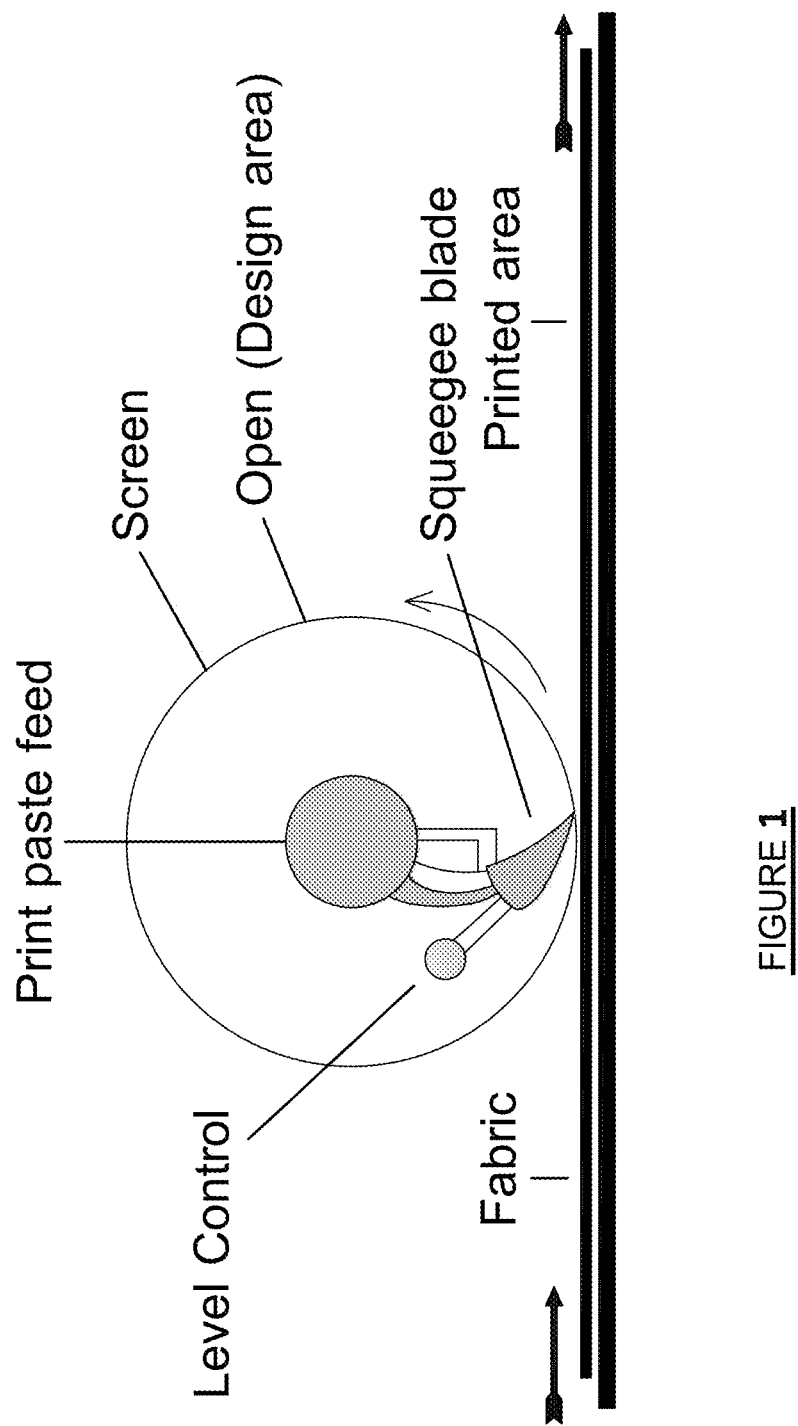
FIG. 1 is a first view of a rotary screen used in textile printing.
Figure 2:
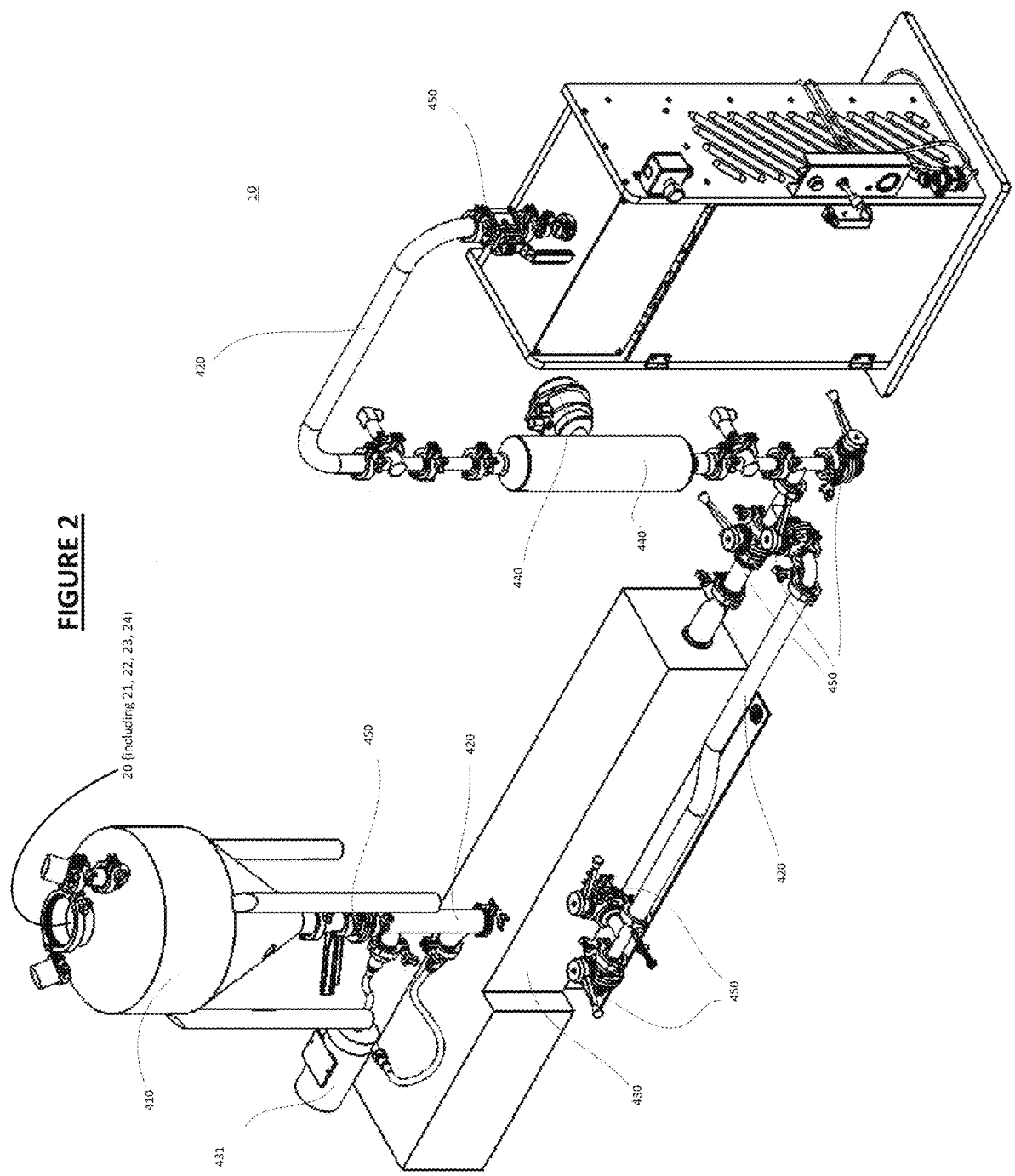
FIG. 2 is a first perspective view of an exemplary drum stencil printing system.
Figure 4B:
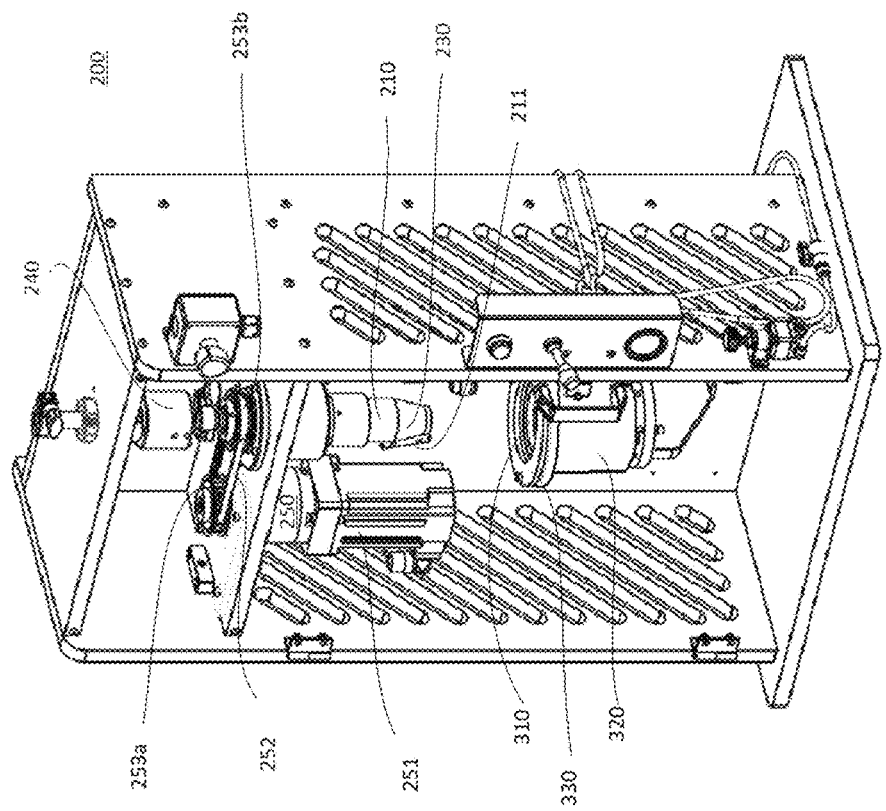
FIGS. 4A and 4B are side and isometric perspective views respectively of an exemplary active printing assembly for use in the drum stencil printing system.
Figure 4A:
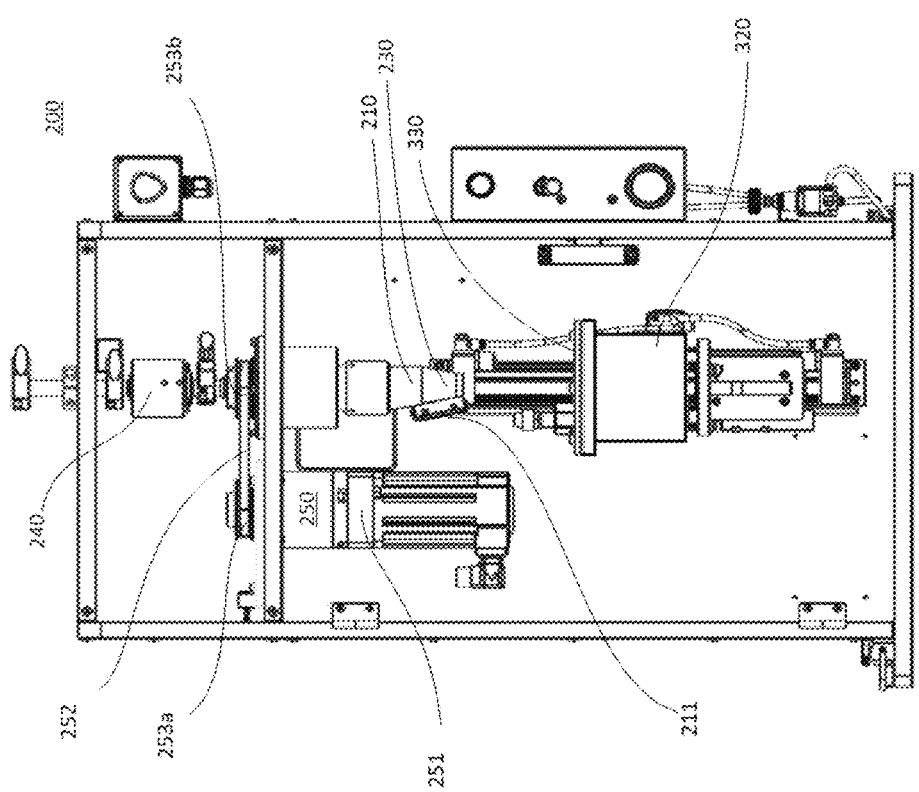

Various embodiments disclosed herein relate to a drum stencil printing system 10. The drum stencil printing system 10 can be incorporated into any production line, including fully automated production lines or hybrid automated/manual production lines. The drum stencil printing system 10 can be integral to a larger production line or may be a separate element that can be installed in series with other automated production equipment.

In some embodiments, the microencapsulated delivery system or its related elements may incorporate features or details including those disclosed in published application US20110177141, published Jul. 21, 2011 and titled "Microencapsulated Delivery System", in published application US200900951641, published Apr. 16, 2009 and titled "Method of Enhancing Beverages by Means of a Unique Microencapsulated Delivery System," in published application US20170119013, published May 4, 2017 and titled "Method of Applying Flavor to Chewing Gum and Edible Substrates", and in U.S. Pat. No. 9,999,864, issued Jun. 19, 2018 and titled "Method of Mixing a Liquid in a Container," each of which is expressly incorporated herein in its entirety and each of which is to be considered a part of the present application.

In the following detailed description, numerous specific details are set forth in order to provide a thorough understanding of the invention. However, the invention may be practiced without these specific details or in any combination incorporating multiple versions of these details together. In other instances, well known methods, procedures, and/or components have not been described in detail so as not to unnecessarily obscure aspects of the invention.

With respect to FIGS. 2-10, in a first embodiment, a drum stencil printing system 10 positions a container 30 for printing a slurry 20, prints the slurry material 20 on a substrate 31 of the container 30, and returns the container 30 to the production line 600. The drum stencil printing system 10 begins by picking up a container 30 (or other substrate 31) from a first position in an assembly line 600 (e.g., selected from a conveyor belt or pulled from a stacked column of containers). An automated positioning element 700 (e.g., a pick-and-place arm) positions each container 30 into a printing cavity 310 of the securing mechanism 300 for securing the container 30 in position during the printing process (e.g., a cup chuck or equivalent element). The active printing assembly 200 inserts into the container 30 secured in the printing cavity 310, and prints the slurry material 20 on the inside surface 31 of the container 30 through an aperture 150 in the drum stencil 100. The primary element of the active printing assembly is the printhead 210, which comprises a nozzle 211 connected by a radial channel 213 to the feed tube 220. The printhead is attached to both an axial extension motor 240, which enables the printhead to insert and retract from the printing cavity 310, and a rotation motor 251, which applies force to rotate the printhead 210 through the rotation belt 252 and rotation gears 253A, 253B. The active printing assembly also comprises the securing mechanism 300, which includes a printing cradle 320 that defines an internal printing cavity 310. A stencil 100 inserted into the printing cavity 310 is secured in place by the pressure applied to the stencil lip 130 between the stencil cradle 320 and the lock plate 330.

When a container 30 is inserted into the printing cavity 310, the stencil 100 is inserted into the concave portion of the container 30, and the printhead 210 extends (either axially or radially) to deflect the pliable drum stencil 100 into contact with the container 30, rotates within the drum stencil 100 to print the slurry 20 inside of the container 30, and retracts to return the stencil 100 to its undeflected position breaking contact between the stencil 100 and the container 30. Once the printhead 210 and stencil 100 are retracted, the container 30 is then removed from the securing mechanism 300 by the automated positioning element 700 and positioned at a second position on the assembly line 600. In some embodiments the second position on the assembly line 600 may be the same as the first position on the assembly line 600, thereby returning the printed container 30 to its original pre-printing position. Multiple drum stencils 100 are carried within a stencil carousel 800, which can include clean drum stencils 100, alternate pattern drum stencils 100B, or specific drum stencils 100 for use with different slurry formulas. When not in use on the active printing assembly 200, other drum stencils 100 may be automatically cleaned by insertion into an automated wash station 900.

In addition to the machinery and process of the printing process, the present invention additionally includes the selection of materials, chemistry, geometry, and physical state of the material 20 to be printed in addition to the substrates 31 on which the material 20 is printed.

The printing method relates to depositing a printing material 20 having either high or low viscosities on a substrate 31 and allowing the material 20 to solidify thereon. When the printing material 20 is printed on the substrate 31, the binder or liquid component 21 of the printing material 20 evaporates, leaving the microcapsules 22 and effervescent material 23 to harden, affixing the printing material 20 to the substrate 31 as dried material 32. When a user pours a desired solvent (e.g., water) over the dried material 32 on the substrate 31, the dried printing material 32 dissolves and the dried printing material 32 mixes with the solvent to form the final beverage or other solution. The printing material or slurry 20 is inherently an element of the present invention.

It is important that the final product, once combined with an intended solvent produces the desired final liquid (e.g., final product or beverage). In the current embodiment, the intended solvent is water and the desired final liquid is a drinkable beverage including flavors, colors, and additives (e.g., caffeine). In other embodiments, the final liquid may include vitamins, minerals, medicines, drugs, flavors, fragrances, dyes or colors, preservatives, extracts, and/or oils.

The slurry 20 should possess beneficial characteristics generally relating to 1) the final characteristics of the dissolved beverage including flavor, fragrance, after taste, mouth-feel, supplements, additives, vitamins, minerals, medicines, proteins, healthiness, bioavailability, carbonation, dyes and colors, and breath freshness; 2) successful, consistent, and speedy printing, binding, and drying on the substrate 31 and operability with the stencil printing system 10; 3) a positive or premium user experience regarding dissolve time, percent slurry dissolved, appearance (e.g., color, shape, height, pattern, and consistency), and reaction with expected solvents; 4) durability to withstand vibration or jostling during transportation and expected environmental temperature and humidity, including potential sustained shelf viability and cupboard shelf-life; and 5) cost, environmental impact, shipping weight, waste-elimination, availability, and flexibility.

In one embodiment, the printing material 20 is a combination of microcapsules 22 and effervescent materials 23 mixed with a binder 21 to form a slurry 20. The slurry 20 may include a protective shell 24 surrounding and preserving some or all of the microcapsules 22 and the effervescent materials 23. The protective shell 24 may be formed of gelatin, sugar, polymers, or other materials suited for encapsulation and spray-drying surrounding and shielding a core including flavors, essences, additives, vitamins, minerals, medicines/drugs, colors or dyes, extracts, oils, and/or supplements. When the dried slurry 32 is exposed to a solvent, the effervescent materials 23 produce additional turbulence and accelerate the rapid dissolution of the microcapsules 22.

When the combination of microcapsules 22, effervescent material 23, and binder 21 (or other carrier) is mixed into its final mixture, the result is a slurry 20 that is viscous and potentially abrasive. In some embodiments, the slurry delivery elements 400 and the entire drum stencil printing system 10 may be capable of mixing, moving, printing, and drying a slurry 20 with a viscosity between 10,000 (ten thousand) and 1,000,000 (one million) centipoise. In some embodiments, the drum stencil printing system 10 may be configured or tuned to mix, move, print, and dry a slurry 20 with a narrower viscosity range. In other embodiments, the drum stencil printing system 10 may be configured or tuned to a slurry 20 that does not fall entirely within the 10,000-1,000,000 centipoise viscosity range without departing from the present invention. Depending on which microcapsules 22 and shells 24 are incorporated in the slurry 20, the mixture may be sensitive to water. The equipment for mixing, storing, and printing with the slurry 20 should be operated and maintained in a manner to minimize potential water contact. The system 10 may be cleaned with ethanol or an ethanol mixture to minimize water retained in the system 10. Additionally, the entire system 10 should be operated in a relatively controlled manufacturing environment maintained within specific temperature and relative humidity ranges. In some embodiments, it may be preferable to operate the drum stencil printing system 10 in an environment that is approximately room temperature with a relative humidity between 5% and 50%; however, the drum stencil printing system 10 may still function outside of these temperature and humidity ranges without departing from the scope of the present invention. The temperature and viscosity of the slurry 20 and the temperature and humidity of the operating environment can be controlled and maintained within preferable ranges to enable and/or optimize slurry mixing, transportation, printing, and drying.

As the slurry 20 is pressed through the apertures 150 of the drum stencil 100, the slurry 20 is printed onto the substrate 31 into a pattern corresponding to the cut-out patterns 150 in the stencil 100. The stencil pattern will be approximately reproduced on the substrate 31 of the container 30. The stencil pattern may be selected to optimize dissolution in the solvent and durability in manufacturing, storage, and shipment. Both the shape and size of each deposited slurry/material 20 element can be individually adjusted. Broader printed elements also allow for thicker printed volumes, which allows for more deposited material; however, broader and thicker printed elements take longer to fully dissolve. The pattern should be selected to optimize the volume of printed material desired against the dissolution time. In some embodiments, a pattern of repeating geometric shapes may be used, such as circles, squares, rectangles, triangles, hexagons, or any other such shape. Because the printed elements are controlled by the stencil 100, more complicated shapes or patterns may also be incorporated, such as unique and recognizable shapes or even product branding or short printed messages on the substrate 31.

In one embodiment, the liquid or solvent is water, and the water dissolves the protective shells 24, activating the microcapsules 22 and effervescent material 23. In other embodiments, other liquids may be used as a solvent, for example, these other liquids may include other organic solvents or compounds, beverages, juice, tonic, club soda, soda, alcohol, liquor, liqueur, tea, coffee, milk, cream, oils, sauces, and/or broths. The slurry 20 may react with different solvents to product different final liquids. Additionally, in some embodiments, the temperature of the solvent may be an important factor contributing to the desired reaction and end-product. For example, in some embodiments, the dried material 32 may dissolve only if the solvent is above a threshold temperature. In still another embodiment, the dried material 32 may dissolve better within a preferred temperature range.

Though the words container, cup, and bowl 30 are used frequently throughout this application, it should be understood that the words container, cup, and bowl are used generally to refer to any shape of substrate 31. While a container 30 inherently includes all variations and geometry of container 30, a person of ordinary skill in the art would additionally understand that other substrates 31 could be used instead of a container 30 without departing from the spirit of the present invention, these potential alternative substrates 31 including but not limited to cups, bowls, cans, jars, canisters, containers, glassware, bottles, beverage pods, pods, plates, pitchers, utensils (including but not limited to spoons, straws, stirrers, forks, sporks, or knives), bags, foils, sheets, wrappers, satchels, cartons, boxes, coolers, and/or sheets, discs, or strips.

The substrate 31—like the slurry 20—should be selected based on its characteristics suitable for 1) successful printing, binding, and drying of the print material 20; 2) durability to withstand vibration or jostling during transportation and expected environmental temperature and humidity, including potential sustained shelf viability and cupboard shelf-life; 3) cost, environmental impact, shipping weight, waste-elimination, availability, and flexibility; and 4) provide a positive or premium user experience with respect to taste, material dissolution, appearance, aesthetic, hand-feel, pliability, durability to withstand expected solvents. Potential characteristics affecting these elements include at least substrate material, substrate dimensions, substrate geometry (including at least height, angle, curvature, and thickness), and substrate 31 processing prior to and/or after printing.

The substrate 31 may additionally be formed from either a single element or from a combination of multiple elements with different characteristics or benefits. In some embodiments, the printing material 20 may first be printed onto a first substrate selected for certain print-related characteristics (e.g., preferential chemical properties or preferential geometry for use with the printing method, or), and that first substrate may then be secured to a second (or any additional number of) substrate(s) providing other desirable properties, including at least the previously mentioned considerations in the prior paragraph or those listed anywhere throughout this application. The multiple substrates may be formed from the same material and/or different materials. The method of securing the first substrate may include mechanical fasteners (e.g., snap-fit), a separate securing element (e.g., adhesives, tapes, screws, rivets), or targeted environmental manipulation (e.g., melting or sonic welding).

As described, the substrate 31 may be constructed from any material to fit the printing process and purpose of the final product. In general, the substrate 31 may be favorably formed from plastics, petroleum-based polymers, biopolymers, hybrid polymers, metals, glasses, and/or papers. In some embodiments, the substrate may desirably be manufactured from one or a combination of plastics, cellulose, paper, polymers manufactured from petroleum or fossil fuels including at least high-density polyethylene (HDPE), low-density polyethylene (LDPE), polyethylene terephthalate (PET), polypropylene (PP), polystyrene (PS), polyvinyl chloride (PVC), and/or polycarbonate (PC), polymers including polylactic acid (PLA) manufactured from sugar and cornstarch, polyhydroxyalkanoate manufactured from corn, Biopolyethylene terephthalate (B-PET) manufactured from a combination of plant and petroleum ingredients. In other embodiments, the substrate 31 may alternatively be formed of metal (for example, but not limited to tin, aluminum, steel, zinc, or copper, any of which may additionally be plated or polymer-coated), glass, or paper (including kraft paper, coated paper, cardboard or corrugated board, offset paper, parchment/baking paper, greaseproof paper, and/or wood pulp, any of which may include recycled elements). In certain embodiments, some or all of the printing substrate 31 may itself be dissolvable and/or edible. The substrate 31 may also include branding or other details directly on the substrate in ink, without affecting the printed/dried slurry 32. In one embodiment, printed ink on the substrate 31 may be preferentially printed on the outside of the substrate 31. It may be preferable to use non-toxic inks in these printed details.

In some embodiments, a specific substrate 31 shape may provide advantages for use with the present drum stencil printing system 10. For example, in some embodiments a container 30 with a thin, angled sidewall presents a better surface for slurry material 20 printing. In some embodiments, a concave container 30 with a flat sidewall angle of between 5 and 20 degrees (as measured from vertical) provides a good surface for the current system 10. More specifically, a concave container 30 with a flat sidewall angle between 10-15 degrees may provide an even more desirable printable surface area for use with the present drum stencil printing system 10. Still more specifically, a concave container 30 with a flat sidewall angle of approximately 12 degrees has been demonstrated to function well with the present drum stencil printing system 10. In some embodiments, the container 30 sidewall is less than 0.02 inches thick. In other embodiments, it may be preferable to print on a substrate 31 that is between 0.008-0.012 inches thick.

The drum stencil printing system 10 includes elements for feeding containers 30 to the active printing assembly 200, the active printing assembly 200 itself, and additional elements for handling the containers 30 after the container 30 has exited the active printing system 200. In some embodiments, the entire system 10 is automated. In other embodiments, only some of the elements of the system 10 are automated, while other steps are manually performed by labor. In some specific embodiments, multiple containers 30 may be simultaneously processed or printed by the drum stencil printing system 10. In other embodiments, only a single container 30 is printed at a time by each drum stencil printing system 10.

Figure 5A:
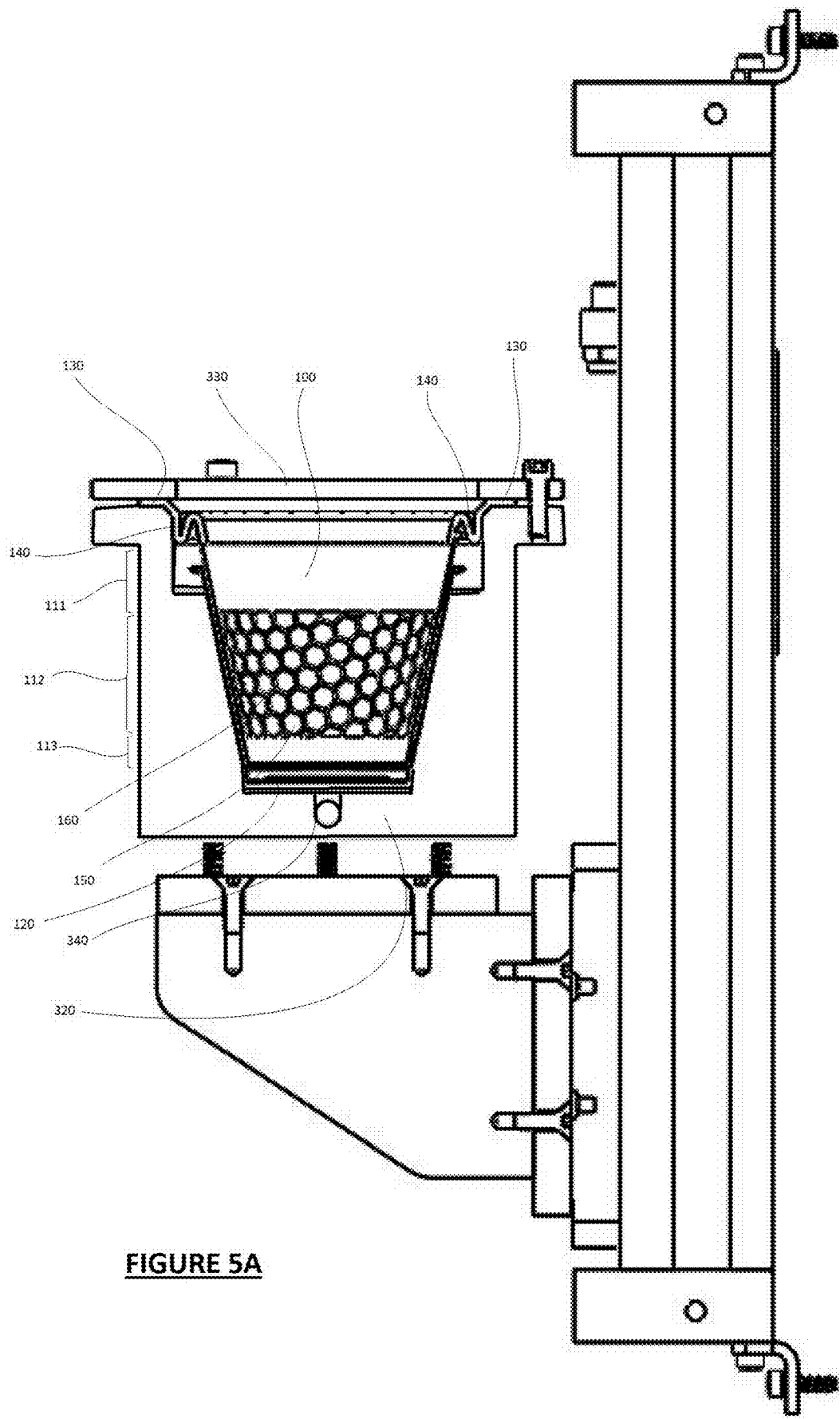
FIG. 5A is a side view of an exemplary drum stencil secured in an exemplary securing mechanism for use in the drum stencil printing system.
Figure 5C:
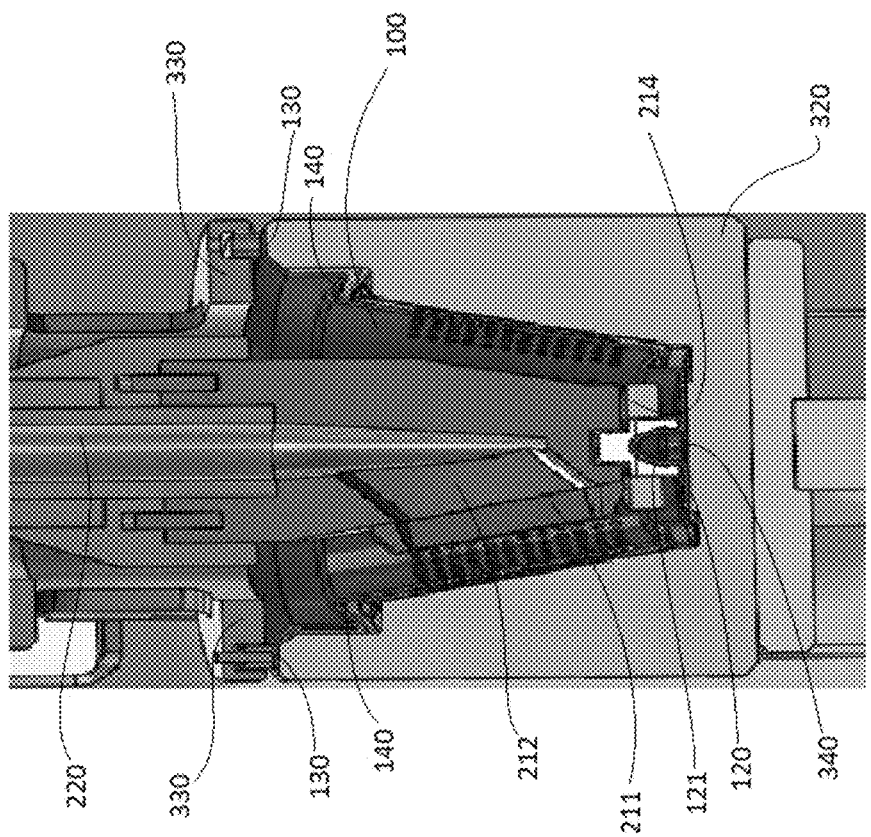
FIGS. 5B and 5C are side cross-section views of an exemplary drum stencil secured within a securing mechanism for use in the drum stencil printing system, depicting a printhead in the partially inserted and fully inserted positions respectively.
Figure 5B:
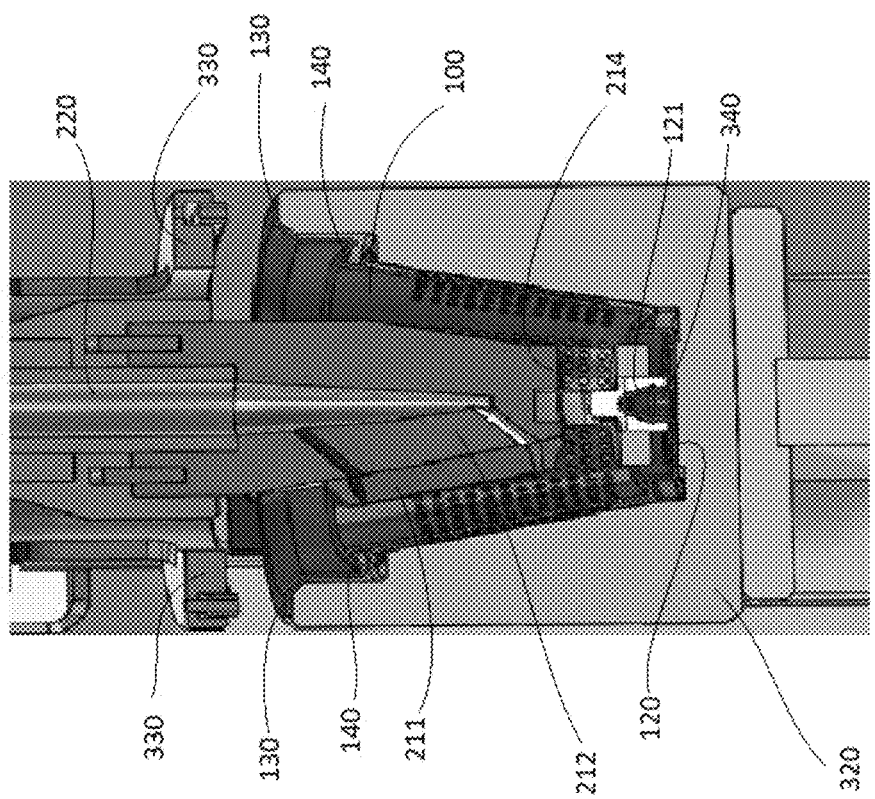
Figure 6:
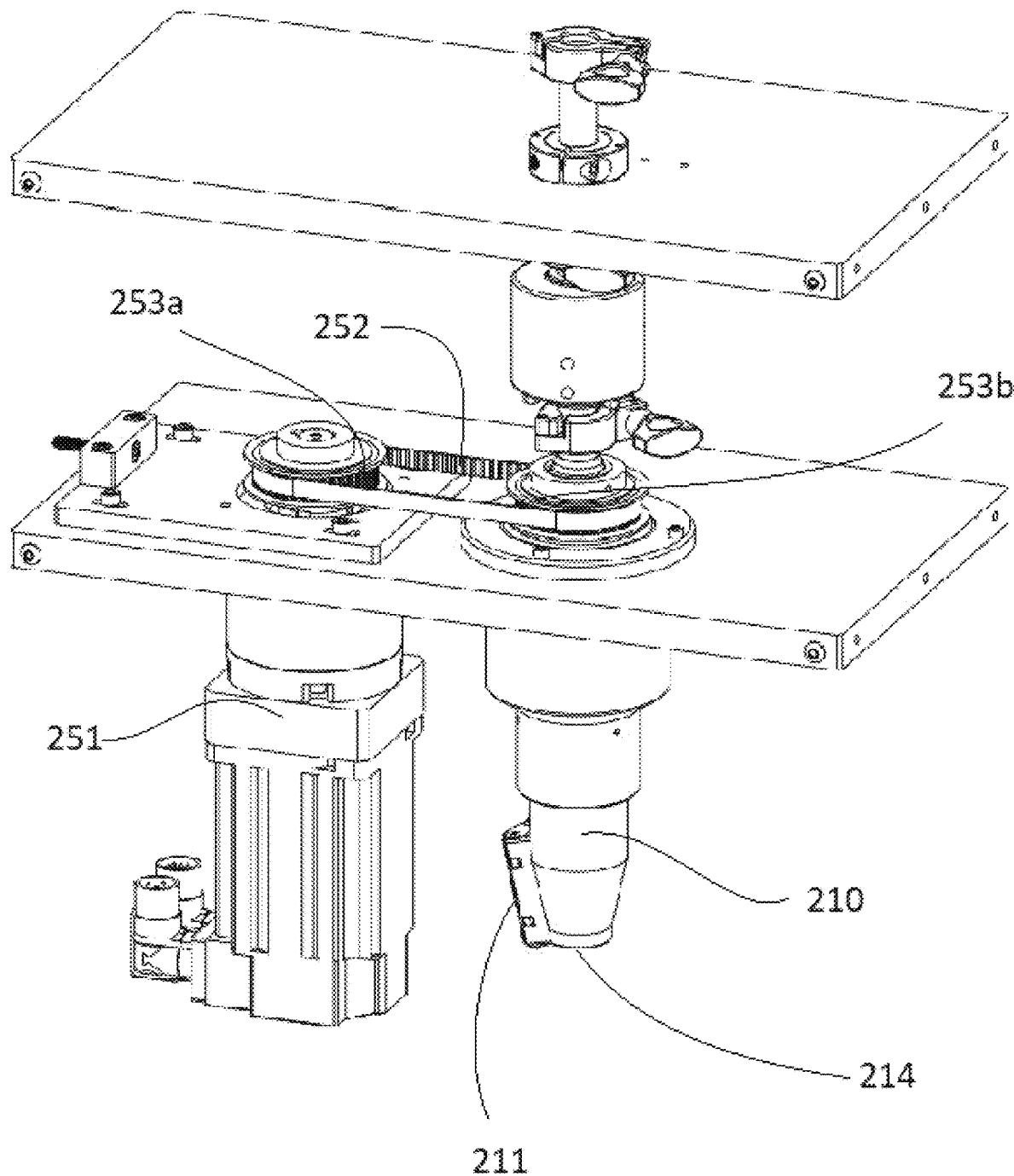
FIG. 6 is an isometric perspective view of a portion of an exemplary slurry delivery element including a printhead for use in the drum stencil printing system.
Figure 9D:
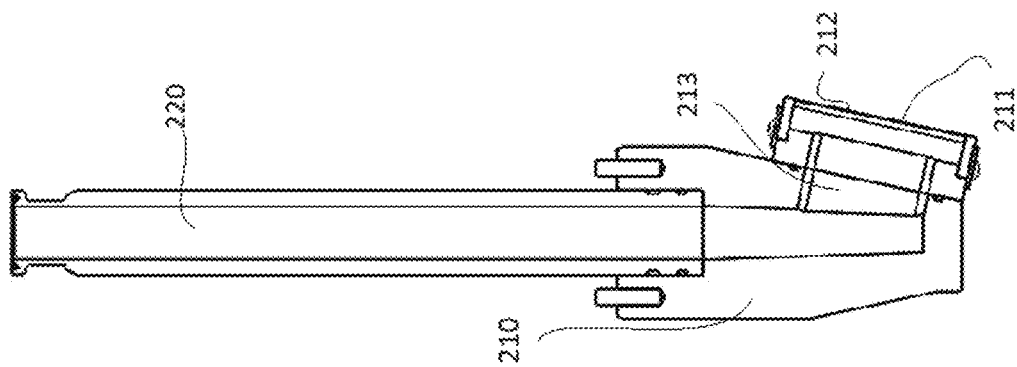
FIGS. 9A, 9B, 9C, and 9D are side, front, isometric perspective, and side cross-section views respectively of an exemplary printhead for use in the drum stencil printing system.
Figure 9C:
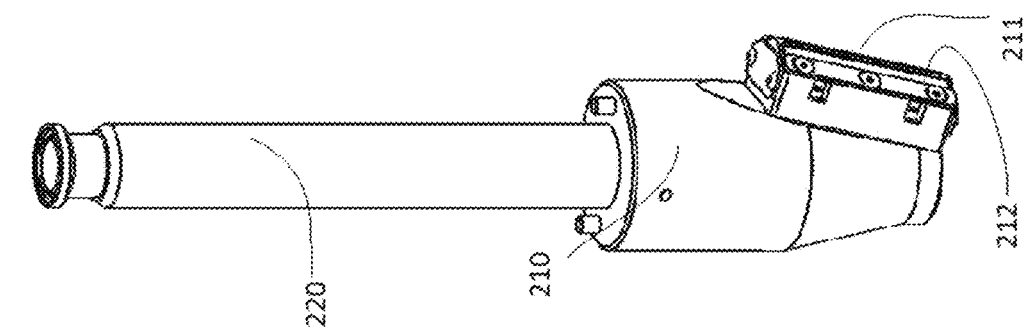
Figure 9B:
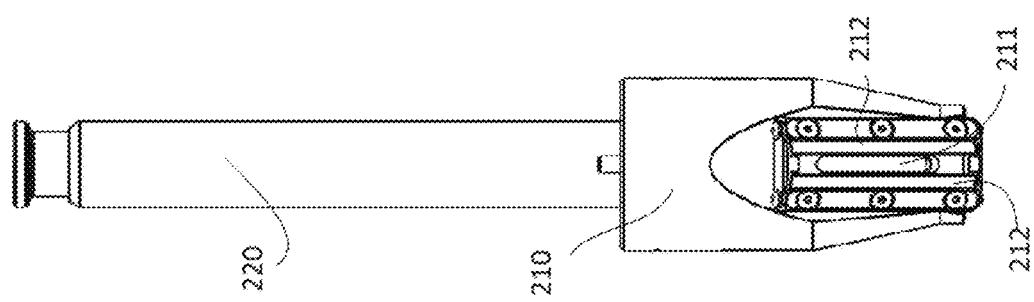
Figure 9A:
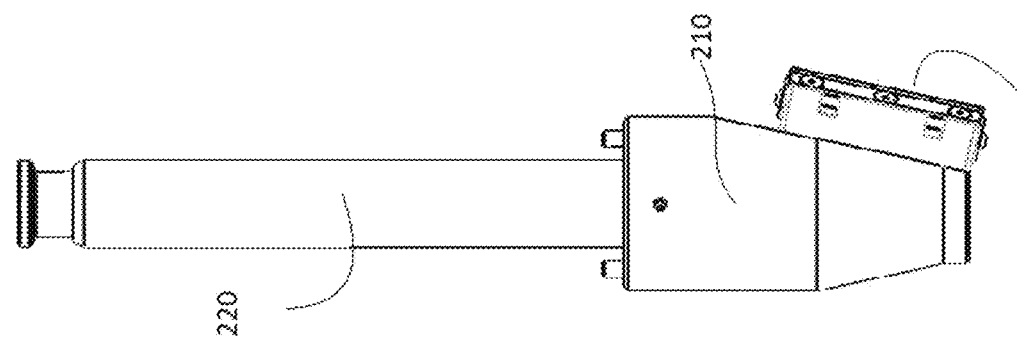
Figure 10:
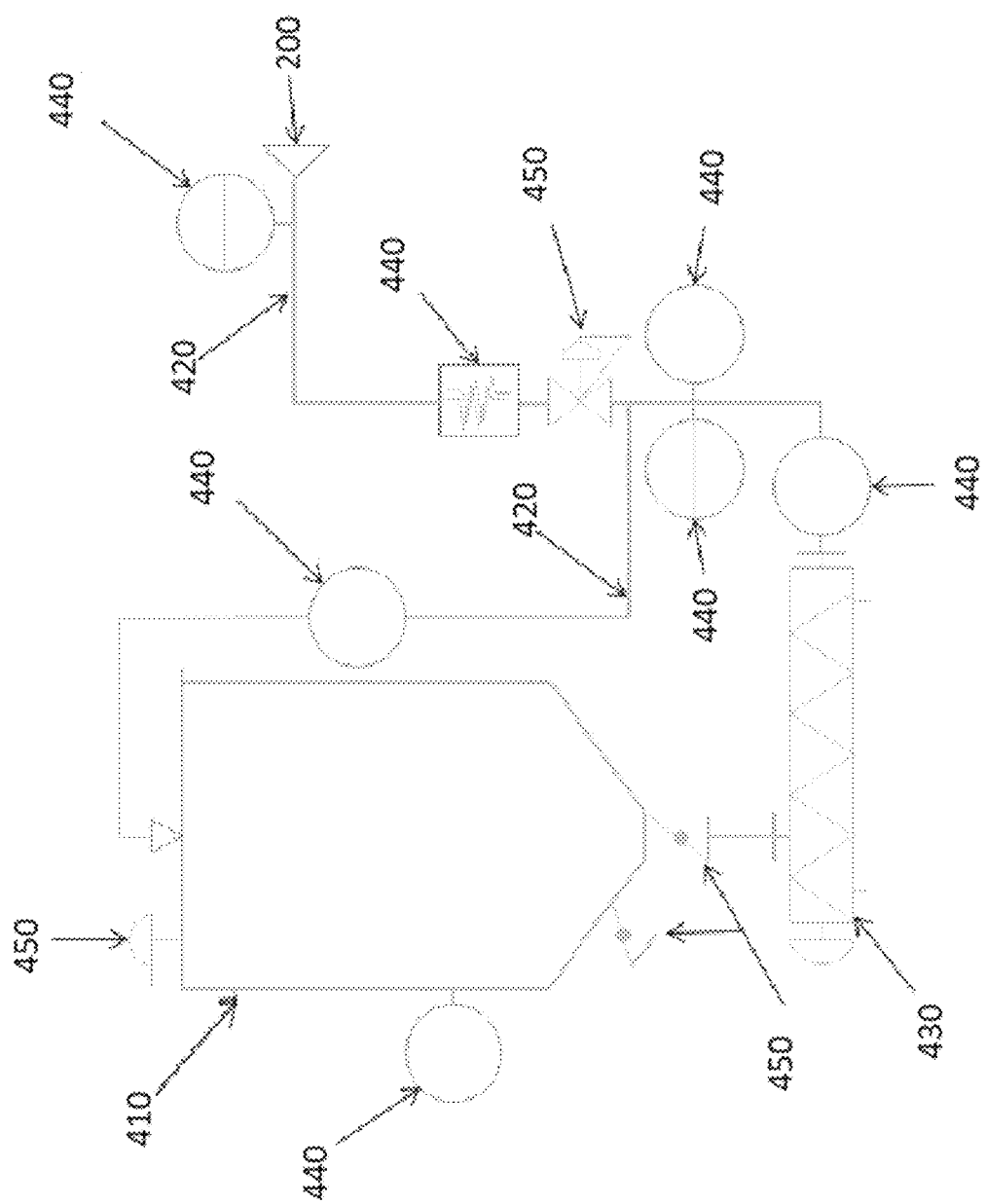
FIG. 10 is a technical diagram of an exemplary configuration of slurry delivery elements for use in the drum stencil printing system.

As shown in FIG. 5A-5C, the drum stencil printing system 10 may include a securing mechanism 300 configured to maintain the container 30 in position during printing by gravity, vacuum, or any method of mechanical engagement, such as a clamp. In one embodiment, the securing mechanism 300 comprises a printing cradle 320 and a lock plate 330. The drum stencil 100 is secured in place by pressure between the lock plate 330 and the printing cradle 320. A container may be inserted into a printing cavity 310 defined by the printing cradle 320. The securing mechanism 300 also comprises a cradle lock 340 configured to secure elements within the printing cradle 310 in place. In the present embodiment, the container 30 and the stencil 100 remain stationary as the printhead 210 moves within the container 30. The benefit of maintaining the container 30 and stencil 100 in a stationary position is that the printed slurry 20 may be more accurately adhered to the container 30 without shaking loose some elements based on the quick acceleration and stop during the print process. In alternate embodiments, the container 30 may be rotated around the printhead 210. In some embodiments, there may be multiple securing mechanisms 300 holding multiple containers 30 in parallel so that a single drum stencil printing system 10 is capable of printing multiple containers 30 simultaneously.

As shown in 5B and 5C, once the container 30 is secured in the printing position (e.g., in the printing cavity 310), the active printing assembly 200 inserts the stencil 100 and printhead 210 into the container 30. The action of inserting the printhead 210 can be accomplished by moving the printhead 210 relative to the container 30, by moving the container 30 relative to the printhead 210, or by moving both the printhead 210 and the container 30 toward each other. This linear or axial motion is driven by the axial extension motor 240. The drum stencil 100 may be positioned between the container 30 and the printhead 210. The printhead 210 applies pressure to the slurry material 20 against the stencil 100 and forces the slurry 20 through the holes 150 in the stencil 100 to adhere to the container 30. The rotation system 250 then rotates the printhead 210 within the drum stencil 100, forcing the slurry 20 through all of the apertures or islands 150 across the entire stenciled portion 112 of the drum stencil.

A significant hurdle to stencil printing a 3-dimensional material to the inside of a concave substrate 31 is that when the stencil 100 is retracted from the interior of the substrate 31, the stencil 100 drags and scrapes off some of the printed material 20 before it dries. It is desirable to maintain the stencil 100 away from both the container 30 sidewall and the printhead 210 of the active printing assembly 200.

As shown in FIGS. 7A through 7C, the inventors have solved this issue in the present invention by both spring-mounting the drum stencil 100 relative to the printhead 210 and utilizing a pliable drum stencil 100. The drum stencil 100 includes an angled stencil sidewall 110 that extends between the lip 130 and the stencil bottom 120. In some embodiments, the stencil sidewall includes a solid upper portion 111 above the stencil patterned portion 112 and a solid lower portion 113 below the stencil patterned portion 112. In some embodiments, the stencil 100 may also include a stencil seam 114. In some embodiments, the stencil bottom 120 may include additional bottom islands and bottom bridges, allowing printing on the bottom of the container 100. The stencil bottom 120 may also include a stencil lock 121 that maintains the stencil 100 in position in the printing cavity 310 during printing. The stencil 100 includes a stencil spring 140, which allows the stencil 100 additional range of motion relative to the printhead 210 and breaks contact between the printhead 210 and the stencil 100 between prints. The pliable drum stencil 100 only makes contact with the substrate 31 walls when a force is applied to deflect the stencil 100. Although the described embodiment incorporates both spring-mounting the stencil 100 relative to the printhead 210 and a pliable drum stencil 100, it should be understood that either feature could be employed separately without departing from the present invention. In some embodiments or uses (such as the embodiment depicted in FIGS. 8A and 8B), a pliable drum stencil 100 might be incorporated without a spring-mount 140 between the stencil 100 and active printing assembly 200, while in some other embodiments or uses a spring-mount 140 between a stencil 100 and active printing assembly 200 might be incorporated without the use of a pliable drum stencil 100.

The stencil 100 including a stencil spring 140 is held off of the printhead 210 by the expansion joint or stencil spring 140 which is positioned between and connects the stencil sidewall 110 to the stencil lip 130, and when the printhead 210 is inserted all the way into the securing mechanism 300, a force applied to the stencil 100 by a portion of the printhead or delivery head 210 may compress the stencil spring or expansion joint 140, bringing the stencil 100 into contact with the printhead 210 (but still maintaining a gap between the stencil 100 and the sidewall of the substrate 31). In one embodiment, the stencil spring 140 is parallel to the axis of the container 30 and securing mechanism 300, so the movement of the stencil 100 relative to the printhead 210 is axial rather than radial. In some embodiments, the stencil 100 may shift 0-1 inch relative to the position of the printhead 210 between its compressed and uncompressed spring 140 positions. In a still more preferable embodiment, the stencil 100 may be maintained between 0.5-0.7 inches away from the printhead 210 in its non-compressed position. The difference between the compressed and uncompressed stencil 100 position may be smaller or larger without departing from the present invention.

When the printhead 210 is retracted from the container, 100 the pressure applied to the stencil spring 140 by the printhead 210 is released, and the printhead 210 again withdraws from the stencil 100, relaxing the stencil spring 140 and retracting the stencil sidewall 110 away from the inner surface of the container 30. As described above, the spring-mounted stencil 100 relative to the printhead 210 could also be used with a rigid stencil 100, preserving some benefits of the present invention.

The stencil 100 is a thin, pliable piece that provides the pattern of apertures 150 and bridges 160 for the printhead 210 to apply the slurry or material 20 to the inside of the container 30. The print pattern desired for the interior of the container 30 may be cut (e.g., laser cut or punched) through the stencil material. The stencil 100 must be thin enough to be easily deflected and so that the holes 150 through the stencil 100 are unlikely to be clogged during or between printing. The stencil 100 must also be smooth enough to minimize the slurry material 20 that bonds to the stencil 100.

The stencil 100 should be constructed of a pliable material that can deflect in response to pressure from the printhead 210 (or a squeegee that is an element of the printhead). The pliable material may include plastic, rubber, metal, or any other material selected for its pliability, durability under repeated stress and movement, and nonstick properties. In some systems, a metal stencil 100 may stand out relative to alternate materials. For example, stainless steel, or more specifically 304 stainless steel may be precision rolled to a desirable thickness for use in this printing application. The stencil 100 could alternatively be constructed of other metals such as aluminum, titanium, brass, zinc, magnesium, or other metals and metallic alloys, including those subsequently coated with anodize, films (including fluorocarbon polymer films), or other surface treatments to enhance performance. Some types of stainless steel have demonstrated superior characteristics for a stencil material. Specifically, a 304 grade of stainless steel has been demonstrated to offer desirable pliability, durability, and nonstick benefits in the present stencil application. Alternatively, the drum stencil 100 could be constructed from thermoset, thermoplastic polymers, elastomeric polymers, or other composite material such as fiber reinforced polymer. In some embodiments, the drum stencil 100 could be made of a polymer, metallic alloy or composite material fabricated from additive manufacturing.

The thickness of the stencil 100 should be selected to optimize the slurry material 20 printing as well as the functionality of the drum stencil printing system 10. A thicker stencil 100 may endure more uses and last longer before needing replacement; however, the added thickness reduces print quality, print consistency, while also requiring additional force from the printhead. In some embodiments, the stencil 100 may preferably be less than 0.2 inches (approximately 5 millimeters) thick so that the stencil 100 is easily deflected, and the slurry 20 does not stick in the stencil holes 150. More specifically, a stencil 100 between 0.025 inches and 0.075 inches (approximately 0.6-2 millimeters) thick offers desirable pliability, print quality, print consistency, and durability without requiring significant force from the printhead 210.

The printhead 210 or squeegee may extend or retract to deflect the stencil 100 to an intended print position. As the printhead 210 or squeegee makes contact with the pliable stencil 100, the stencil 100 deflects to make contact with the printing surface's inner sidewalls. After the printhead 210 or squeegee passes by a point on the stencil 100, the stencil 100 returns to its original, undeflected position, pulling away from the inner sidewall of the printing substrate 31. This stencil 100 restoration allows the printing surface of the substrate 31 to be removed from the stencil 100 without dragging or smearing the pattern deposited on the printing surface of the substrate 31.

While the pliable stencil 100 is inside of the printing cavity 310 of the securing mechanism 300, the stencil 100 is maintained between 0-0.1 inches away from the container sidewall. For example, in one exemplary embodiment, a container substrate 31 approximately 0.01 inch thick may be maintained approximately 0.055 inches away from a 0.04 inch thick stencil 100 when the printhead 210 is fully inserted into the printing cavity 310. The rotating printhead 210 then deflects the stencil 100 to contact the container substrate 31 as the slurry material 20 is forced against the stencil 100 and through the apertures 150, thereby applying the slurry material 20 against the substrate 31. When the printhead 210 passes a section of the stencil 100 and substrate 31, the stencil 100 returns to its undeflected position slightly removed from the substrate 31, leaving the printed slurry material 20 in place and undisturbed on the substrate 31.

In an alternate embodiment (not shown), a rigid drum stencil 100 could still be incorporated into the present system without departing from the present invention. A drum stencil 100 smaller in radius than the substrate 31 radius could be shifted to contact the substrate 31 by pressure from the printhead 210 or squeegee, so that all other portions of the rigid drum stencil 100 are not in contact with the container 30. If the printhead 210 or squeegee then retracts, the rigid drum stencil 100 can return to a central position along the central axis of the active print assembly 200, so that no part of the rigid drum stencil 100 is in contact with the container 30.

In some embodiments of the present invention, the drum stencil printing system 10 includes a carousel or caddy 800 of multiple drum stencils 100. In some embodiments, the system 10 is configured to automatically remove a first drum stencil 100A from the active printing assembly 200, place the first drum stencil 100A in the stencil carousel 800, select a second drum stencil 100B from the stencil carousel 800, and attach the second drum stencil 100B to the active printing assembly 200 so that the system 10 can quickly swap between multiple stencils 100. In some embodiments the stencils 100 in the carousel 800 may have different patterns or thicknesses selected to pair well with specific slurries 20 in use. In other embodiments, the stencils 100 in the carousel 800 may be more or less identical, but may be swapped to allow the system 10 to clean, protect, or maintain stencils 100 against grime, contamination, residue build-up, or repetitive stress failures. The stencils 100 may also be scanned or examined either automatically or manually to detect damage or clogs.

In some embodiments of the present invention, the drum stencil printing system 10 additionally includes a stencil wash station 900. A stencil 100 may be removed from the active printing assembly 200 and automatically washed before either returning to the active printing system 200 or being deposited in the stencil carousel or caddy 800. The automatic wash station 900 may use heat, pressurized air, pressurized liquid, water bath, alcohol bath, temperature manipulation, mechanical abrasion, or any combination thereof to clean the stencils 100.

The active printing assembly 200 is connected to a slurry delivery system 400. In some embodiments, the slurry delivery element comprises a slurry pump 430 driven by a pump motor 431 to press slurry 20 from the slurry tank or slurry mixer 410 through the slurry delivery lines 420 and ultimately to the feed tube 220 and nozzle 211 of the printhead 210, where the slurry 20 is ultimately applied through the drum stencil 100 to the substrate 31. The slurry delivery system 400 includes a number of sensors and valves, including temperature sensors, pressure sensors, Coriolis sensors, flow sensors, release valves, and butterfly valves to monitor and control the behavior and consistency of the slurry 20 as it travels through the slurry delivery lines 420.

The delivery head 210 may be positioned at the distal end 214 of the slurry delivery lines 420 (from the slurry tank 410) and directly delivers the slurry 20 through the nozzle 211 against the stencil 100 and through the apertures 150 onto the substrate 31. In other embodiments, the delivery head 210 may be positioned along the feed tube 220 short of the distal end 214. The delivery head 210 may include a flow halt mechanism 230 that stops the flow of slurry 20 between printing containers 30. As the slurry pump 430 applies pressure to the slurry material 20 through the slurry delivery lines 420 and feed tube 220, slurry 20 is pressed past the flow halt mechanism 230 and out of the nozzle 211 and through the drum stencil apertures 150. The pressure forces the slurry 20 through the drum stencil 100 and onto the container 30 in whatever pattern the stencil 100 creates. The delivery head 210 rotates within the stencil 100, applying the slurry 20 across the entire stenciled portion 112. In the present embodiment, the printhead 210 rotates relative to the feed tube 220; however, in alternate embodiments, it may be preferable to rotate the printhead 210 and feed tube 220 together to minimize unintentional shearing or cavitation in the slurry 20. In some embodiments, when the stencil spring 140 is compressed between the printhead 210 and the container 30 or securing mechanism 300, the printhead 210 is in contact with the drum stencil 100. When the stencil spring 140 is not compressed, the printhead 210 draws away from the stencil 100.

In the present embodiment, the printhead 210 comprises a radial channel 213 that extends radially from the feed tube 220, including a thin and tall nozzle 211, the elongate shape of the nozzle 211 enabling the printhead 210 to extrude a consistent, vertical strip of slurry material 20 through the stencil 100 as the printhead 210 rotates. A larger cross section enables the nozzle 211 of the printhead 210 to print more of the substrate 31 surface at one time, but it can be more difficult to supply constant pressure of slurry 20 across the entire nozzle 211 area. Conversely, a smaller cross section for the nozzle 211 of the printhead 210 enables the system 10 to more accurately control pressure and print consistency across the entire surface area, but at the cost of reduced print surface (meaning that more time is necessary to print the desired surface). Further, a smaller nozzle 211 cross section may require more slurry pressure from the slurry pump 430. Though not required, a nozzle 211 cross section less than 1 square inch may beneficially balance these two concerns. It may be further beneficial to use a nozzle 211 with a cross section between 0.3 and 0.5 square inches. The back edge 212 of the delivery head's nozzle 211 acts as a sort of squeegee, pressing the supplied slurry 20 through the apertures 150 in the stencil 100 and collecting any would-be excess slurry 20 that would otherwise be left on the inside of the stencil 100, eliminating waste.

It is preferable for the delivery nozzle 211 to be at least as tall as the desired printing area 112 through the stencil 100, which enables the printhead 210 to supply slurry 20 equally across the entire stencil pattern 112 during a single rotation. The printhead 210 should be set at a vertical angle approximately equal to the sidewall angle of the substrate 31 that is being printed. For example, a substrate 31 that is 12 degrees off vertical may be used with a contact end that is also approximately 12 degrees off vertical to maximize contact and even printing pressure across the entire stencil patterned area 112.

Although the present embodiment describes a rotating printhead 210 within a stationary stencil 100 and stationary substrate 31, in an alternate embodiment (not shown) the printhead 210 may be held stationary while the stencil 100 and substrate 31 rotate around the fixed printhead 210 or squeegee. The benefits of a stationary substrate 31 and stencil 100 with a rotating printhead 210 include increased print quality and consistency due to the reduced movement of the printed container 30 during printing. Alternatively, at least one benefit of incorporating a stationary printhead 210 with a moving container 30 and moving stencil 100 is that the printhead mechanism 210 is significantly less complicated and less likely to experience mechanical breakdown.

Although the present embodiment describes a printhead nozzle 211 for printing the sidewall or substrate 31 of a container 30, in alternate embodiments, a printhead nozzle 211 may be employed for printing the bottom of a container 30. In still other embodiments, a single nozzle 211 may match the curvature or angle of a container, cup, bowl 30, or other substrate 31, enabling a single nozzle 211 (or multiple nozzles working simultaneously in a single system) to print the sidewalls and bottom of the substrate 31 simultaneously.

Another alternate embodiment to the enclosed printhead 210 is to use an open printhead (not shown), which comprises a slurry deposit chamber, fed by the slurry feed tube 220 from the slurry pump 430 and slurry tank 410. Rather than controlling the slurry 20 flowrate carefully, as with a closed printhead 210, the open printhead employs a squeegee to mechanically press slurry 20 from the slurry deposit chamber through the stencil 100. The mechanical barrier between the open printhead squeegee and the stencil 100 controls the deposit of slurry 20 on the container sidewall 31. An open printhead is less precise and consistent in its printing and may generate more waste and build-up in the system 10; however, the benefit of an open printhead is that the flow of slurry 20 from the slurry pump 430 through the slurry delivery lines 420 and feed tube 220 does not have to be as precisely controlled.

The printhead 210 and entire active printing assembly 200 may include flow halt mechanisms 230 to stop slurry 20 flow between each print. The flow halt mechanism 230 may comprise a physical barrier, such as a gate or door that mechanically opens and closes to specifically start and stop the flow of slurry as desired. In another embodiment, the flow halt mechanism 430 is a deformable elastomeric element near the nozzle 211. Slurry pressure applied to the deformable elastomeric element causes the element to deform, creating an opening and allowing the slurry 20 to flow. The physical barrier may be positioned at the printhead or anywhere along the feed tube 220 or slurry delivery lines 420. Alternatively, the flow halt mechanism 230 may selectively manipulate slurry pressure at the printhead 210 so that slurry 20 is only extruded when desired.

In some embodiments, a printhead carousel or caddy (not shown) and a printhead wash station (not shown) similar to the stencil carousel or caddy 800 and stencil wash stations 900 described previously may be employed for similar benefits to the printheads 210. Either different or generally identical printheads 210 may be swapped from the printhead carousel or caddy between different slurries 20 or substrates 31 or to allow for cleaning and/or maintenance. The printhead wash station may quickly flush a printhead 210 with air, water, alcohol (e.g., ethanol, isopropyl, or other alcohols) or may use mechanical scrubbing or temperature manipulation (or any combination thereof) to clean and sterilize the printheads. After cleaning, the printhead 210 may either be returned from the printhead wash station to the active printing assembly or instead deposited on the printhead carousel or caddy while another printhead 210 is selected for use.

After the container 30 or substrate 31 is removed from the active printing system 200, the slurry 20 needs to set/dry and solidify. The low environmental humidity helps to accelerate this process; however, the drying may be accelerated or otherwise aided by adjusting the temperature or atmospheric pressure for the drying containers 30. The system 10 may apply heat through convection, radiant heat, or microwave, and any of these heating systems may be vacuum assisted. Alternatively, the printed slurry may be dried quicker through a chemical process. Once the slurry 20 has dried onto the substrate 31, the dried material 32 is secured to the substrate 31 and can be moved with less concern for disturbing and damaging the printed material 32. The system 10 may also employ rotary evaporators and/or alcohol recapture systems to collect and recycle or reuse the alcohol evaporating from the drying slurry on the printed containers.

The slurry 20 is transported from a slurry tank or mixer 410 through the slurry delivery lines 420, and the slurry flow from the slurry tank or mixer 410 to the print head 210 is monitored and controlled by pumps 430, sensors 440, valves 450, and other elements. The slurry 20 from the tank or mixer 410 is pressed to and through the printhead 210. In the present embodiment, a feed tube 220 tapers as it approaches the printhead/delivery head 210. The delivery head nozzle 211 is connected to the tapered portion of the feed tube 220 by a radial channel 213. The shape and angle of the feed tube 220, the taper angle of the feed tube 220 as it approaches the delivery head 210, the cross section of the radial channel 213, and the cross section and shape of the nozzle 211 all have an effect on the slurry pressure within the tube feed 220 and slurry delivery lines 420 and coming from the nozzle 211. With the viscous material 20 printed in the presently described embodiment, a feed tube 220 approximately 0.625 inches in diameter, gradually tapering at approximately a 5-degree angle down to a 0.21 diameter at the delivery section maintains pressure and consistency throughout the feed tube 220 and produces a desirable print. However, the feed tube 220 could be constructed or swapped out with elements having alternate dimensions or angles without departing from the spirit of the present invention. In some embodiments, the feed tube would not need to taper at all. Additionally, in some embodiments used to print the base of the container, cup, or bowl, the channel from the feed tube to the nozzle may be axial rather than radial.

In some embodiments, the printhead 210 mechanically extends and retracts. An axial extension motor 240 drives the extension and retraction of the printhead 210. When the printhead 210 extends, it makes contact with the drum stencil 100, while in its retracted state, the printhead 210 is not in contact with the drum stencil 100, and the drum stencil is not in contact with the container 20. In other embodiments, the printhead 210 may be removed and replaced with interchangeable parts. Interchangeable printheads 210 allows the elements to be rotated and cleaned to manufacture nearly continuously without significant cleaning delays. Additionally, different printheads 210 may have different dimensions designed for different slurries, different drum stencils 100, and different container 30 geometries. Additionally, in some embodiments a first printhead 210 may be used for printing the sidewalls of a container 30 while a second printhead is used to print the bottom of the container 30. The two printheads 210 may be used by separate active printing assemblies 200 that are used in series. In one embodiment, the same slurry 20 is used for both the container sidewall and container bottom prints. In other embodiments, a different slurry may be used for the sidewalls of the container 30 and the bottom of the container 30.

The slurry 20 is generally a viscous and abrasive mixture, so it is important to use durable materials like stainless steel anywhere the system 10 may contact the slurry 20 throughout the printing system 10. It is also important to incorporate easily cleaned, repaired, and/or replaced parts due to the potential long-term abrasive effect of the slurry mixture 20.

One or more of the features illustrated in the figures or described in the specification and claims may be rearranged and/or combined into a single component or embodied in several components. Additional components may also be added without departing from the invention. It is to be understood that some terms are used interchangeably in this description.

Although elements of this invention are discussed as an automated drum stencil printing system 10, the included functional elements could be easily incorporated into other systems without departing from the invention. It should be readily apparent that the same elements described with respect to the described embodiments could be employed in any of these other form factors with only minor variations without departing from the spirit of the present invention.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A drum stencil printing system for printing on a concave surface, the drum stencil printing system comprising:
    a securing mechanism configured to maintain a substrate having a concave surface in a secured position;
    a pliable drum stencil comprising a rigid stencil connected by a flexible elastomer to the drum stencil printing system, the drum stencil being configured to be inserted into the concave surface of the substrate when the substrate is maintained in the secured position; and
    a rotating printhead positioned inside of the pliable drum stencil configured to print a slurry through the rigid stencil of the drum stencil onto the concave surface of the substrate;
    wherein the radial distance between the printhead and the rigid stencil of the drum stencil is decreased as the drum stencil inserts into the concave surface;
    wherein the flexible elastomer of the drum stencil enables pressure applied by the printhead on the rigid stencil to displace the rigid stencil to make contact with the substrate at the point where the printhead is printing the slurry through the rigid stencil;
    wherein the flexible elastomer of the drum stencil enables the rigid stencil to return to an undisplaced position out of contact with the substrate when the printhead is not applying pressure to the drum stencil.

2. The drum stencil printing system of claim 1, wherein the rigid stencil of the drum stencil comprises a metallic alloy frame.

3. The drum stencil printing system of claim 1, wherein the drum stencil printing system is configured to print a slurry with a viscosity between 10,000 and 1,000.00 centipoise (cP) on the substrate.

4. The drum stencil printing system of claim 1, wherein the flexible elastomer of the drum stencil comprises thermoset, thermoplastic, elastomeric polymer, a composite material such as fiber reinforced polymer, or a combination thereof.

5. The drum stencil printing system of claim 1, wherein the rigid stencil of the drum stencil comprises a metallic alloy such as steel, aluminum, titanium, brass, zinc, magnesium, including those subsequently coated with anodize, film, or other surface treatment to enhance performance.

6. The drum stencil printing system of claim 1, wherein the rigid stencil of the drum stencil is a frustoconical stencil and is configured to insert into a frustoconical substrate.

7. A drum stencil printing system for printing on a concave surface, the drum stencil printing system comprising:
- a securing mechanism configured to maintain a substrate having a concave surface in a printing position;
- a pliable drum stencil comprising a rigid stencil connected by a flexible elastomer to the drum stencil printing system; and
- a printhead configured to be inserted inside of the drum stencil configured to print a slurry through the drum stencil onto the concave surface of the substrate.

8. The drum stencil printing system of claim 7, wherein the printhead rotates within the drum stencil as it presses the slurry through the rigid stencil of the drum stencil onto the substrate.

9. The drum stencil printing system of claim 8, wherein the printhead applies a pressure to the drum stencil, deflecting the rigid stencil of the drum stencil to be in contact with the substrate at the point where the printhead is printing the slurry through the rigid stencil of the drum stencil and the undeflected areas of the rigid stencil of the drum stencil are not in contact with the substrate.

10. The drum stencil printing system of claim 7, wherein the radial distance between the printhead and the rigid stencil of the drum stencil is decreased as the drum stencil inserts into the concave surface.

11. The drum stencil printing system of claim 7, wherein the flexible elastomer of the drum stencil comprises thermoset, thermoplastic, elastomeric polymer, a composite material such as fiber reinforced polymer, or a combination thereof.

12. The drum stencil printing system of claim 7, wherein the rigid stencil of the drum stencil comprises a metallic alloy such as steel, aluminum, titanium, brass, zinc, magnesium, including those subsequently coated with anodize, film, or other surface treatment to enhance performance.

13. The drum stencil printing system of claim 7, wherein the drum stencil comprises a polymer, metallic alloy, composite material, a composite material such as fiber reinforced polymer, or a combination thereof fabricated from additive manufacturing.

14. The drum stencil printing system of claim 7, wherein the drum stencil printing system is configured to print a slurry with a viscosity between 10,000 and 1,000,000 centipoise (cP) on the substrate.

15. The drum stencil printing system of claim 14, wherein the drum stencil printing system prints a slurry comprising a combination of two or more materials, including at least a first material that is suspended in the slurry and at least a second material that is dissolved in the slurry.

16. The drum stencil printing system of claim 14, wherein the drum stencil printing system prints a slurry comprising a combination of two or more materials, wherein the first material and the second material are both suspended in the slurry, and none of the materials are dissolved in the slurry.

17. The drum stencil printing system of claim 7, wherein the drum stencil printing system prints a slurry comprising a combination of two or more materials, wherein the first material and the second material are both partially or fully dissolved in the slurry, and none of the materials are suspended in the slurry.

18. The drum stencil printing system of claim 7, wherein the printhead applies a pressure to the drum stencil, deflecting the flexible elastomer of the drum stencil to be so that the rigid stencil is in contact with the substrate at the point where the printhead is printing the slurry through the rigid stencil.

19. The drum stencil printing system of claim 18, wherein the flexible elastomer of the drum stencil enables the rigid stencil to return to an undeflected position out of contact with the substrate when the printhead is not applying pressure to the drum stencil.

20. The drum stencil printing system of claim 7, wherein the rigid stencil of the drum stencil is a frustoconical stencil and is configured to insert into a frustoconical substrate.

* * * * *